(12) United States Patent
Wisniewski et al.

(10) Patent No.: US 6,649,584 B2
(45) Date of Patent: Nov. 18, 2003

(54) CLEANING WIPE

(75) Inventors: Karen Wisniewski, Bound Brook, NJ (US); Barbara Thomas, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/412,909

(22) Filed: Apr. 14, 2003

(65) Prior Publication Data

US 2003/0195132 A1 Oct. 16, 2003

Related U.S. Application Data

(63) Continuation of application No. 10/346,673, filed on Jan. 17, 2003, now Pat. No. 6,586,385, which is a continuation-in-part of application No. 10/241,203, filed on Sep. 11, 2002, now Pat. No. 6,551,980, which is a continuation of application No. 10/159,554, filed on May 31, 2002, now Pat. No. 6,534,472, which is a continuation-in-part of application No. 10/086,165, filed on Feb. 27, 2002, now Pat. No. 6,432,904, which is a continuation-in-part of application No. 10/008,715, filed on Nov. 13, 2001, now Pat. No. 6,440,925.

(51) Int. Cl.$^7$ .............................................. C11D 17/00
(52) U.S. Cl. ................. 510/438; 510/255; 510/424; 510/428; 510/495; 510/501; 510/503; 510/505; 134/42; 428/288; 424/70.28; 15/209.1
(58) Field of Search ................. 510/438, 295, 510/499, 501, 503, 505, 424, 428; 134/42; 428/288; 424/70.28; 15/209.1

(56) References Cited

U.S. PATENT DOCUMENTS

| | | | | |
|---|---|---|---|---|
| 4,725,489 A | * | 2/1988 | Jones et al. | 428/289 |
| 5,141,803 A | * | 8/1992 | Pregozen | 428/288 |
| 6,340,663 B1 | * | 1/2002 | Deleo et al. | 510/438 |
| 2002/0031486 A1 | * | 3/2002 | Lunsmann et al. | 424/70.28 |
| 2003/0119705 A1 | * | 6/2003 | Barnabas et al. | 510/438 |

\* cited by examiner

*Primary Examiner*—Necholus Ogden
(74) *Attorney, Agent, or Firm*—Richard E. Nanfeldt

(57) ABSTRACT

A dishwashing cleaning wipe comprising a fabric wherein the fabric is impregnated with a cleaning composition.

2 Claims, No Drawings

CLEANING WIPE

RELATED APPLICATION

This application is a continuation in part application of U.S. Ser. No. 10/346,673 filed Jan. 17, 2003 now U.S. Pat. No. 6,586,385 which in turn is a continuation in part application of U.S. Ser. No. 10/241,203 filed Sep. 11, 2002 now U.S. Pat. No. 6,551,580 which in turn is a continuation in part application of U.S. Ser. No. 10/159,554 filed May 31, 2002 now U.S Pat No. 6,534,472 which in turn is a continuation in part application of U.S. Ser. No.10/086,165 filed Feb. 27, 2002 now U.S. Pat. No. 6,432,504 which in turn is a continuation in part application of U.S. Ser. No. 10/008,715 filed Nov. 13, 2001 now U.S. Pat. No. 6,440,925.

FIELD OF INVENTION

The present invention relates to a dishwashing cleaning wipe which is single or multi layer fabric substrate which has been impregnated with a liquid cleaning composition.

BACKGROUND OF THE INVENTION

The patent literature describes numerous wipes for both body cleaning and cleaning of hard surfaces but none describe wipes for cleaning dishware, flatware, pots and pans. U.S. Pat. Nos. 5,980,931, 6,063,397and 6,074,655 teach a substantially dry disposable personal cleansing product useful for both cleansing and conditioning the skin and hair. U.S. Pat. No. 6,060,149 teaches a disposable wiping article having a substrate comprising multiple layers.

U.S. Patent Nos. 5,756,612; 5,763,332; 5,908,707; 5,914,177; 5,980,922 and 6,168,852 teach cleaning compositions which are inverse emulsions.

U.S. Pat. Nos. 6,183,315 and 6,183,763 teach cleaning compositions containing a proton donating agent and having an acidic pH. U.S. Pat. Nos. 5,863,663; 5,952,043; 6,063,746 and 6,121,165 teaches cleaning compositions which are oil in water emulsions.

SUMMARY OF THE INVENTION

A single use cleaning wipe for dishwashing application comprises a water insoluble substrate, with a cleaning composition containing at least one anionic surfactants and water coated onto and/or impregnated into the water insoluble substrate.

The liquid cleaning compositions of this invention are not an emulsion and do not contain potassium sorbate, a polysaccharide polymer, a polycarboxylate polymer, polyvinyl alcohol polymer, polyvinylpyrrolidone polymer or methyl vinyl ether polymer.

DETAILED DESCRIPTION OF THE INVENTION

The present invention relates to a cleaning wipe for dishware, flatware, pots and pans which comprises approximately:

(a) 20 wt. % to 95 wt. % of a water insoluble substrate; and
(b) 5 wt. % to 85 wt. % of a liquid cleaning composition being coated onto and/or impregnated into said water insoluble substrate, wherein said liquid cleaning composition comprises:
  (i) 0 wt. % to 60 wt. %, more preferably 8 wt. % to 40 wt. % of at least one anionic surfactant selected from the group of sulfate anionic surfactants and sulfonated anionic surfactants and mixtures thereof;
  (ii) 0.25% to 30% of a surfactant selected from the group consisting of amine oxides, alkyl polyglucosides, zwitterionic surfactants, ethoxylated nonionic surfactants and alkanol amides and mixtures thereof; and
  (iii) the balance being water, wherein the composition has a pH of 6 to 8 and does not contain ammonium hydroxide, an alkali metal hydroxide, potassium sorbate, a polysaccharide polymer, a polycarboxylate polymer, polyvinyl alcohol polymer, polyvinylpyrrolidone polymer or methyl vinyl ether polymer.

Suitable water-soluble non-soap, anionic surfactants used in the instant compositions include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, ammonium, magnesium and mono-, di- or tri-$C_2$–$C_3$ alkanolammonium, with the sodium, magnesium and ammonium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is a mixture of an alkali metal ammonium salt and an alkaline earth metal salt of a linear alkyl benzene sulfonate having a high content of 3- (or higher) phenyl isomers and a correspondingly low content (well below 50%) of 2- (or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an α-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735,096.

Examples of satisfactory anionic sulfate surfactants are the alkali metal or ammonium salt $C_8$–$C_{18}$ alkyl sulfate salts the ethoxylated $C_8$–$C_{18}$ alkyl ether sulfate salts having the formula $R(OC_2H_4)_n OSO_3M$ wherein n is 1 to 12, preferably 1 to 5, and M is a metal cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the ethoxylated alkyl ether sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. The ethoxylated alkyl ether sulfates differ from one another in the number of moles of ethylene oxide reacted with one mole of alkanol. Preferred alkyl sulfates and preferred ethoxylated alkyl ether sulfates contain 10 to 16 carbon atoms in the alkyl group.

The ethoxylated $C_8$–$C_{12}$ alkylphenyl ether sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic surfactants are the $C_9$–$C_{15}$ alkyl ether polyethenoxyl carboxylates having the structural formula $R(OC_2H_4)_nOX$ COOH wherein n is a number from 4 to 12, preferably 5 to 10 and X is selected from the group consisting of

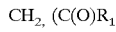

and

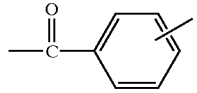

wherein $R_1$ is a $C_1$–$C_3$ alkylene group. Preferred compounds include $C_9$–$C_{11}$ alkyl ether polyethenoxy (7–9) C(O) $CH_2CH_2COOH$, $C_{13}$–$C_{15}$ alkyl ether polyethenoxy (7–9)

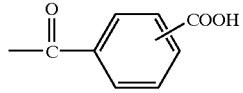

and $C_{10}$–$C_{12}$ alkyl ether polyethenoxy (5–7) CH2COOH. These compounds may be prepared by condensing ethylene oxide with appropriate alkanol and reacting this reaction product with chloracetic acid to make the ether carboxylic acids as shown in U.S. Pat. No. 3,741,911 or with succinic anhydride or phthalic anhydride. Obviously, these anionic surfactants will be present either in acid form or salt form depending upon the pH of the final composition, with salt forming cation being the same as for the other anionic surfactants.

The instant composition can optionally include 0.1 wt. % to 15 wt. % of a water-soluble zwitterionic surfactant, which can also be used provides good foaming properties and mildness to the present nonionic based liquid detergent. The zwitterionic surfactant is a water soluble betaine having the general formula:

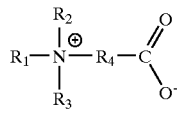

wherein $R_1$ is an alkyl group having 10 to 20 carbon atoms, preferably 12 to 16 carbon atoms, or the amido radical:

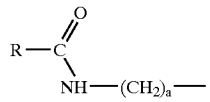

wherein R is an alkyl group having 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia)acetate, coco dimethyl betaine or 2-(N-coco N, N-dimethylammonio)acetate, myristyl dimethyl betaine, palmityl dimethyl betaine, lauryl diemethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine.

The instant composition can include an amine oxide semi-polar nonionic surfactants comprise compounds and mixtures of compounds having the formula:

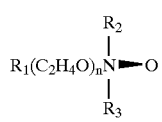

wherein $R_1$ is an alkyl, 2-hydroxyalkyl, 3-hydroxyalkyl, or 3-alkoxy-2-hydroxypropyl radical in which the alkyl and alkoxy, respectively, contain from 8 to 18 carbon atoms, $R_2$ and $R_3$ are each methyl, ethyl, propyl, isopropyl, 2-hydroxyethyl, 2-hydroxypropyl, or 3-hydroxypropyl, and n is from 0 to 10. Particularly preferred are amine oxides of the formula:

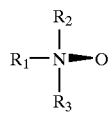

wherein $R_1$ is a $C_{12-16}$ alkyl and $R_2$ and $R_3$ are methyl or ethyl. The above ethylene oxide condensates, amides, and amine oxides are more fully described in U.S. Pat. No. 4,316,824 which is hereby incorporated herein by reference.

The instant composition can include a $C_{12-14}$ alkyl monoalkanol amide such as lauryl monoalkanol amide or a $C_{12-14}$ alkyl dialkanol amide such as lauryl diethanol amide or coco diethanol amide.

The water soluble nonionic surfactants utilized in this invention are commercially well known and include the primary aliphatic alcohol ethoxylates, secondary aliphatic alcohol ethoxylates, alkylphenol ethoxylates and ethyleneoxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic detergent class includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9–15 carbon atoms, such as $C_{11}$ alkanol condensed with 9 moles of ethylene oxide (Neodol 1-9), $C_{12-13}$ alkanol condensed with 6.5 moles ethylene oxide (Neodol 23-6.5), $C_{12-15}$ alkanol condensed with 7 or 3 moles ethylene oxide (Neodol 25-7 or Neodol 25-3), $C_{14-15}$ alkanol condensed with 13 moles ethylene oxide (Neodol 45-13), and the like. Such ethoxamers have an HLB (hydrophobic lipophilic balance) value of about 8 to 15 and give good O/W emulsification, whereas ethoxamers with HLB values below 8 contain less than 5 ethyleneoxide groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of EO per mole of nonyl phenol, dinonyl phenol condensed with about 12 moles of EO per mole of phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

Also among the satisfactory nonionic detergents are the water-soluble condensation products of a $C_8$–$C_{20}$ alkanol with a heteric mixture of ethylene oxide and propylene oxide wherein the weight ratio of ethylene oxide to propylene oxide is from 2.5:1 to 4:1, preferably 2.8:1 to 3.3:1, with the total of the ethylene oxide and propylene oxide (including the terminal ethanol or propanol group) being from 60–85%, preferably 70–80%, by weight. Such detergents are commercially available from BASF-Wyandotte and a particularly preferred detergent is a $C_{10}$–$C_{16}$ alkanol condensate with ethylene oxide and propylene oxide, the weight ratio of ethylene oxide to propylene oxide being 3:1 and the total alkoxy content being about 75% by weight.

Condensates of 2 to 30 moles of ethylene oxide with sorbitan mono- and tri-$C_{10}$–$C_{20}$ alkanoic acid esters having a HLB of 8 to 15 also may be employed as the nonionic detergent ingredient in the described composition. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

Other suitable water-soluble nonionic detergents which are less preferred are marketed under the trade name "Pluronics." The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L 62 and L 64.

The alkyl polysaccharides surfactants, which can be used at a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4-positions rather than at the 1-position, (thus giving e.g. a glucosyl or galactosyl as opposed to a glucoside or galactoside). However, attachment through the 1-position, i.e., glucosides, galactoside, fructosides, etc., is preferred. In the preferred product the additional saccharide units are predominately attached to the previous saccharide unit's 2-position. Attachment through the 3-, 4-, and 6-positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula $$R_2O(C_nH_{2n}O)r(Z)_x$$

wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferable 0; and x is from 1.5 to 8, preferably from 1.5 to 4, most preferably from 1.6 to 2.7. To prepare these compounds a long chain alcohol (R$_2$OH) can be reacted with glucose, in the presence of an acid catalyst to form the desired glucoside. Alternatively the alkyl polyglucosides can be prepared by a two step procedure in which a short chain alcohol (R$_1$OH) can be reacted with glucose, in the presence of an acid catalyst to form the desired glucoside. Alternatively the alkyl polyglucosides can be prepared by a two step procedure in which a short chain alcohol (C$_{1-6}$) is reacted with glucose or a polyglucoside (x=2 to 4) to yield a short chain alkyl glucoside (x=1 to 4) which can in turn be reacted with a longer chain alcohol (R$_2$OH) to displace the short chain alcohol and obtain the desired alkyl polyglucoside. If this two step procedure is used, the short chain alkylglucosde content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is APG 625 glycoside manufactured by the Henkel Corporation of Ambler, Pa. APG25 is a nonionic alkyl polyglycoside characterized by the formula:

$$C_nH_{2n+1}O(C_6H_{10}O_5)_xH$$

wherein n=10 (2%); n=122 (65%); n=14 (21–28%); n=16 (4–8%) and n=18 (0.5%) and x (degree of polymerization)= 1.6. APG 625 has: a pH of 6 to 10 (10% of APG 625 in distilled water); a specific gravity at 25° C. of 1.1 g/ml; a density at 25° C. of 9.1 lbs/gallon; a calculated HLB of 12.1 and a Brookfield viscosity at 35C, 21 spindle, 5–10 RPM of 3,000 to 7,000 cps.

The instant composition can optionally contain 0.1 wt. % to 10 wt. % of a polyethylene glycol is depicted by the formula:

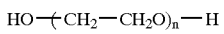

wherein n is about 8 to about 225, more preferably about 10 to about 100,000, wherein the polyethylene glycol has a molecular weight of about 200 to about 1,000. One preferred polyethylene glycerol is PEG1000 which is a polyethylene glycol having a molecular weight of about 1000.

The water is present in the composition at a concentration of about 5 wt. % to 70 wt. %.

The product of the present invention comprises a water insoluable substrate with one or more layers. Each layer may have different textures and abrasiveness. Differing textures can result from the use of different combinations of materials or from the use of different manufacturing processes or a combination thereof. A dual texture substrate can be made to provide the advantage of a more abrasive side for cleaning difficult to remove soils. A softer side can be used for fine dishware and flatware. The substrate should not dissolve or break apart in water. It is the vehicle for delivering the cleaning composition to dishware, flatware, pots and pans. Use of the substrate enhances lathering, cleaning and grease removal.

A wide variety of materials can be used as the substrate. It should have sufficient wet strength, abrasivity, loft and porosity. Examples include, non woven substrates, wovens substrates, hydroentangled substrates and sponges.

Examples of suitable non woven water insoluable substrates include, 100% cellulose Wadding Grade 1804 from Little Rapids Corporation, 100% polypropylene needlepunch material NB 701-2.8-W/R from American Nonwovens Corporation, a blend of cellulosic and synthetic fibres-Hydraspun 8579 from Ahlstrom Fibre Composites, and &0% Viscose/30% PES Code 9881 from PGI Nonwovens Polymer Corp.

Another useful substrate is manufactured by Jacob Holm-Lidro Rough. It is a composition material comprising a 65/35 viscose rayon/polyester hydroentangled spunlace layer with a hydroenlongated bonded polyeser scribbly layer.

Still another useful substrate is manufactured by Texel "TI". It is a composite material manufactured from a layer of coarse fiber 100% polypropylene needlepunch, an absorbent cellulose core and a fine fiber polyester layer needlepunched together. The polypropylene layer can range from 1.5 to 3.5 oz/sq. yd. The cellulose core is a creped paper layer ranging from 0.5 to 2 oz./sq. yd. The fine fiber polyester layer can range from 0.5 to 2 oz./sq. yd.

Still another composite material manufactured by Texcel from a layer of coarse fiber 100% polypropylene needlepunch layer, an absorbent cellulose core and a fine fiber polyester layer needlepunched together. The polypropylene layer can range from 1.5 to 3.5 oz/sq. yd. The cellulose core is a creped paper layer ranging from 0.5 to 2 oz/sq. yd. The fine fiber polyester layer can range from 0.5 to 2 oz/sq. yd. The polypropylene layer is flame treated to further increase the level of abrasivity. The temperature of the flame and the length of time the material is exposed can be varied to create different levels of surface roughness.

The abrasiveness is tested by cutting one quarter inch thick Lucite boards to fit an abrader bed. The boards are marked to indicate the track of the wipes during abrasion (approximately 2¼ and 4½ inches from one long edge) and three spots along the track (6, 9 and 12 inches from the short end). This gives unique and reproducible locations at which to do gloss measurements which are in the center of the abrasion track.

Using a BYK-Gardener Haze-Gloss glossmeter, the indicated spots are measured for starting gloss. An average and standard deviation is reported for each track using the three measurements.

Pieces of the wipes are cut approximately 3 inches by 2 inches. This piece is wrapped around a piece of sponge that fits in a holder for the abrader. (Indication should be made of whether the material is being used in the machine or cross direction). This wrapped sponge is placed in the holder, tucking all the edges of the wipe into the holder so that it is kept firmly in place. The dry sponge is wetted with approximately 20–25 g of water (either deionized, distilled or tap as the experiment desires). This is done so that there are two wipes in the trial.

The gloss measured Lucite board is placed in the abrader bed. Set the abrader for 500 cycles and start.

After the abrader cycles have ended, the Lucite board is removed. It is wiped dry with paper towel to remove any residual water. It is also inspected for any fingerprints incurred during handling and these are also wiped clean. Remeasure the gloss at the specified spots again and again report the average of these three spots and the standard deviation for each track.

The higher the abrasiveness of the wipe, the more that it roughens the surface of the Lucite and the more the gloss is reduced. The most abrasive of the wipes therefore give the greatest decrease in gloss. Results for this test are given below.

| Material (all machine direction) | Change in Gloss for 500 cycles |
| --- | --- |
| 3 layer needlepunch (Texel) no flame treatment | 0 |
| 3 layer needlepunch (Texel) medium flame treatment | 4 |
| 3 layer needlepunch (Texel) high flame treatment | 19 |

Ahlstrom Manufacturers:

A hydroentangled nonwoven created from a blend of cellulosic and polyester and/or polypropylene fibers with an abrasive side. The basis weight can range from 1.2 to 6 ounces per square yard.

A composite dual textured material manufactured by Kimberly Clark comprises a coarse meltblown polypropylene, polyethylene, or polyester and high loft spunbond polyester. The two materials can be laminated together using chemical adhesives or by coprocessing the two layers. The coarse meltblown layer can range from 1 to 3 ounces per square yard while the highloft spunbond layer can range from 1 to 3 ounces per square yard.

Another example of a composite is a dual textured material composed of coarse meltblown polypropylene, polyethylene, or polyester and polyester/cellulose coform. The two materials can be laminated together using chemical adhesives or by coprocessing the two layers. The coarse meltblown layer can range from 1 to 3 ounces per square yard. The coform layer can range in composition from 30% cellulose and 70% polyester to 70% cellulose and 30% polyester and the basis weight can range from 1.5 to 4.5 ounces per square yard.

The product of the present invention comprising mutliple layers may be ultrasonically bonded after applying the coating of one or more of the layers. Alternatively layers may be bonded together by needlepunch, thermal bonding, chemical bonding, or sonic bonding prior to applying the coating and/or impregnation.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following cleaning wipes were made:

| Ingredient | A | B | C | D | E | F |
| --- | --- | --- | --- | --- | --- | --- |
| Ammonium ethoxylated alkyl ether sulfate | 29.1 | 18.6 | | | 23.5 | 17.4 |
| Sodium linear alkyl benzene sulfonate | | | 26.2 | 21.2 | 26.4 | 19.5 |
| Lauramide myristamide monoethanol amide | | 7.6 | | 8.8 | | 8.7 |
| Ethanol | | 13.3 | | | | |
| Water | Bal. | Bal. | Bal. | Bal. | Bal. | Bal. |

All formulas were coated onto and impregnated into a Texel "T1" nonwoven. The amount of formula used was between 7 and 14 g per 6.75"×8" wipe (0.13 to 0.26 g/sq in or for an average basis weight per wipe of 5.2 g, 135 to 269% add on).

All formulas produced foam when wet under the tap and could readily be used to wash a dish.

What is claimed:

1. A dishwashing cleaning wipe which comprises approximately:
   (a) 15 wt. % to 95 wt. % of a water insoluble substrate having more than one layer; and
   (b) 5 wt. % to 85 wt. % of a liquid cleaning composition being coated onto said water insoluble substrate, wherein said liquid cleaning composition comprises:
      (i) 8 wt. % to 60 wt. % of at least one anionic sulfonate surfactant selected from the group consisting of sulfonated anionic surfactants and sulfated anionic surfactants;
      (ii) 0.25% to 30% of lauramide myristamide monoethanolamide; and
      (iii) the balance being water wherein the composition has a pH of 6 to 8 and is not an emulsion and does not contain ammonium hydroxide, an alkali metal hydroxide, potassium sorbate, a polysaccharide polymer, a polycarboxylate polymer, polyvinyl alcohol polymer, polyvinylpyrrolidone polymer or methyl vinyl ether polymer.

2. A wipe according to claim 1, wherein said water insoluble substrate comprises a coarse polypropylene layer, an absorbent cellulose core and a fine fiber polyester layer.

* * * * *